United States Patent [19]

Reardon, Jr. et al.

[11] 4,067,886
[45] Jan. 10, 1978

[54] PROCESS FOR THE PREPARATION OF SELECTIVELY AND SYMMETRICALLY DI-HALOGENATED KETALS

[75] Inventors: Robert C. Reardon, Jr., Tenafly; Eddie N. Gutierrez, Fort Lee, both of N.J.

[73] Assignee: Lever Brothers Company, New York, N.Y.

[21] Appl. No.: 611,364

[22] Filed: Sept. 8, 1975

Related U.S. Application Data

[63] Continuation of Ser. No. 426,854, Dec. 20, 1973, abandoned.

[51] Int. Cl.$^2$ .................. C07B 9/00; C07C 41/00
[52] U.S. Cl. .................. 260/340.7; 260/338; 260/340.9 R; 260/611 R; 260/611 A; 260/615 A; 260/694

[58] Field of Search ............ 260/340.9, 340.7, 611 R, 260/611 A, 615 A, 694, 338

[56] References Cited

U.S. PATENT DOCUMENTS

| | | | |
|---|---|---|---|
| 3,453,290 | 7/1969 | Propper | 260/340.9 |
| 3,824,292 | 7/1974 | Kirby | 260/615 A X |
| 3,919,328 | 11/1975 | Gutierrez et al. | 260/615 A |

Primary Examiner—Richard L. Raymond
Attorney, Agent, or Firm—Kenneth F. Dusyn; James J. Farrell; Melvin H. Kurtz

[57] ABSTRACT

A method is disclosed wherein selectively halogenated ketals are prepared by treating ketones and ketals with halogen in an organic solvent under conditions of ordinary temperature and pressure. This process obviates the need for extreme times, temperatures, and complex equipment while resulting in higher yields than obtained heretofore.

9 Claims, No Drawings

PROCESS FOR THE PREPARATION OF SELECTIVELY AND SYMMETRICALLY DI-HALOGENATED KETALS

This is a continuation of application Ser No. 426,854, filed Dec. 20, 1973, now abandoned.

BACKGROUND OF THE INVENTION

1. Field of the Invention

This invention pertains to a new and improved method for the preparation of selectively halogenated ketals and ketones, more specifically selectively chlorinated or brominated ketals and ketones.

2. Description of the Art

Heretofore, it has been extremely difficult to obtain selectively halogenated ketones and ketals. The formation of halogenated ketals has been reported to occur by reaction of halogenated ketones with alcohols in a patent to Morey U.S. Pat. No. 2,374,494, and Dittli et al in Bull. Soc. Chim. Fr. 1968, 4208, by the reaction of vinyl ethers or esters with alkyl hypochlorite as exemplified by Cass U.S. Pat. No. 2,433,890, Weissermel et al German Patent No. 1,053,487, Shostakovskii et al Akad. Nauk SSSR., otdel Khim. Nauk 1953, 1043, and Filachione, U.S. Pat. No. 2,411,826, or by the direct halogenation of ketals, Anselm et al German Pat. No. 639,507, Dusseau et al, Rec. Trav. Chim. Pays-Bas 1970, 535 and Field, J. Am. Chem. Soc. 83, 3504. The first two methods suffer from one or more of the following deficiencies; two step synthesis, use of very low temperatures and low yields. The third method generally suffers from use of inconvenient or relatively expensive reaction systems, e.g. dimethylformamide (DMF) or sulfur dioxide ($SO_2$) as a solvent, use of metal alcoholates and use of low temperatures.

It is even more difficult to obtain selectively and symmetrically dihalogenated ketones and ketals. This is so because of the natural tendency, once the monohalogenated compound has been formed, of the second halogen to substitute onto the same carbon as the first halogen. Previous attempts to form selective and symmetrical dihalogenated ketones and ketals have usually resulted in the use of excessive amounts of halogenating agents, extreme temperatures and pressures as well as complex equipment. An example of some of the problems encountered by the art is illustrated by Jones, U.S. Pat. No. 2,204,135, however, his solution involves the use of corrosive materials. Rahrs, U.S. Pat. No. 2,235,562, proposed another solution involving chlorinating ketones in the vapor phase and utilizing complex cooling equipment. It can readily be seen that all this is obviated by the instant invention.

SUMMARY OF THE INVENTION

The novel process for the preparation of selectively halogenated ketals and ketones involves the following reaction sequences (although the reaction sequences illustrate chlorine, bromine reacts similarly):

A. Chlorination of Ketones To Chlorinated Ketals

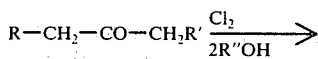

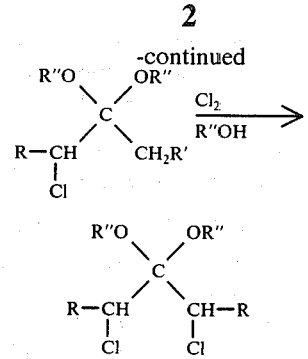

B. Chlorination of Ketals

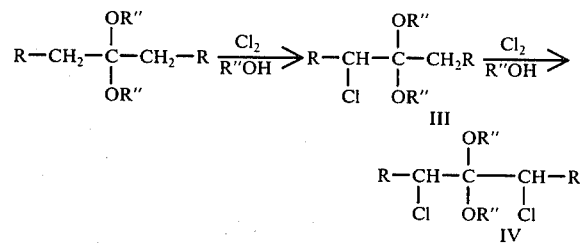

These chlorinated products may be hydrolyzed under acid conditions to produce chlorinated ketones as shown in the following typical example:

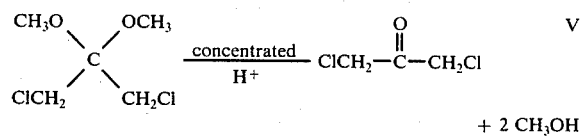

$$+ \; 2 \; CH_3OH$$

The method of the instant invention has the advantage in that it effects selective, step-wise halogenation as demonstrated in the above reaction sequences. The process is selective in that only the carbon atoms alpha to the ketal group (as in reaction scheme B) or alpha to the carbonyl group (as in reaction scheme A) are halogenated. The process is also step-wise in that monohalogenated products are obtained almost exclusively by introducing one mole of halogen to one mole of substrate. The process is additionally selective in yet another sense; that is upon introduction of a second mole of halogen, halogenation of the already-formed monohalogenated ketals (I and III) occurs primarily at the remaining unhalogenated alpha carbon atoms. Although there is some reaction at the initially halogenated alpha carbon, it is to a lesser degree than that at the unhalogenated carbon. Thus, the method provides a novel way of obtaining symmetrically dihalogenated ketals and ketones. Surprisingly, it has been found that when the symmetrical isomer has been formed, it will not react any further. However, the unsymmetrical isomer will continue to react.

The method of the present invention is conveniently carried out by slowly bubbling halogen gas through an alcoholic solution of the ketone or of the ketal at room temperature and atmospheric pressure. The method requires no special apparatus. All that is required is control of the halogen being introduced and stirring. Reactions are typically short in duration, give products of high purity, produce no undesirable products of decomposition and are nearly quantitative based on molecular halogen.

The major advantage of this method over the prior art is that the latter discloses no efficient means of producing selectively halogenated ketals or ketones from the corresponding unhalogenated compounds. Another advantage is the simplicity of the chemical system required to produce the results described.

DESCRIPTION OF THE INVENTION

This invention relates to a process for the preparation of selectively halogenated ketals and ketones. The process is selective in that only carbon atoms that are alpha to the carbonyl or ketal group are halogenated. Another surprising feature is that when a straight chain ketone or ketal is treated according to the process of this invention the selectivity persists regardless of the chain length. Additionally, the selectivity will persist where the ketal or ketone being treated is one having a mixed structure, i.e. a straight chain portion and another portion comprising either a branched chain or some type of ring structure. The halogenation will take place predominately on the straight chain portion of the compound and substitute at the carbon alpha to the ketal or carbonyl group.

It is our belief, although not intending to be bound by such, that both the selectivity and degree of halogenation obtained by the instant invention are due to steric hindrance. Steric hindrance, of course, is the nonoccurrence of an expected chemical reaction, due to inhibition by a particular atomic grouping. The steric hindrance is present, initially, in the ketal itself by virtue of the alkoxy groups present in the compound. This steric hindrance causes the reaction to take place at the alkyl portion of the molecule. As previously exemplified, when the starting material is a ketone the ketal is formed during the reaction, thus giving rise to the necessary steric hindrance. The second role played by steric hindrance relates to the degree of halogenation. Where the starting ketone or ketal is a straight chain compound, the product obtained by the instant process is a symmetrically dihalogenated ketal. When the starting material is of mixed structure the resultant product is a monohalogenated ketal. In both instances, the products are selectively halogenated and also can be acid hydrolyzed to the respective halogenated ketones.

Accordingly, it is an object of this invention to provide a method of preparing selectively and symmetrically dihalogenated ketals which comprises treating with a halogen selected from the group consisting of chlorine and bromine compounds of the formula:

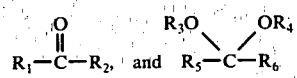

wherein each of $R_1$, $R_2$, $R_5$, and $R_6$ is a straight chain alkyl group of from 1 to 20 carbon atoms, $R_3$ and $R_4$ are a straight chain alkyl group of from 1 to 20 carbon atoms, $R_3$ and $R_4$ may further be taken together to form a ring having from 2 to 4 carbon atoms; said treatment being in an organic solvent selected from the group consisting of monohydric and polyhydric alcohols wherein the ratio of said solvent to ketone or ketal is from about 5/1 to about 20/1 and at a temperature of from about 0° C to about 80° C.

It is a further object of the invention to prepare selectively monohalogenated ketals wherein the halogenation takes place at the carbon atoms alpha to the ketal or carbonyl group.

It is an additional object of the invention to obtain in high yields selectively halogenated ketones and ketals, without the use of extreme reaction conditions and complex equipment.

It is also an object of the invention to provide a more economical and feasible method for the preparation of compounds which find use as pesticides, plasticizers, and fungicides, as fiber modifying agents and as resinification agents in the formation of resinous aromatic hydrocarbons.

The novel process of the instant invention may be exemplified as follows:

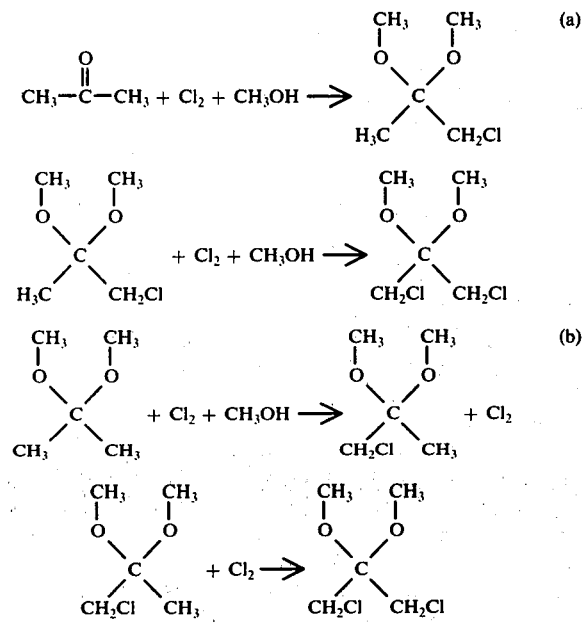

The halogenated ketals produced by either of (a) or (b) may be subsequently hydrolyzed under acid conditions to produce dihalogenated ketones. What has been illustrated above are two general routes for the formation of selectively and symmetrically chlorinated ketals. The first involves chloroketalization of ketones whereas the second involves the direct chlorination of ketals. Although chlorine has been illustrated, bromine may also be used as well with similar results.

While we do not wish to be bound by any particular mechanism, it is our view that the use of an alkanol containing only C—H groups to which the —OH groups are attached prevents the ketal from decomposing into a ketone and the alcohol. Accordingly, it is essential to the present invention that there be an excess of the alcohol relative to the starting ketal or ketone, said ratio being at least 5 to 1, preferably from about 5:1 to about 20:1 in favor of the alcohol.

The halogenation of the ketal results in a compound that is sterically hindered, e.g.

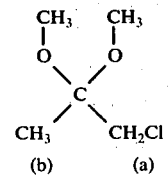

By virtue of such steric hindrance, the next halogen substitution will take place primarily at (b). As a matter of fact, what is believed to be occurring simultaneously are the following reactions, as illustrated in the case of a ketone. The reaction commences with the formation of the monohalogenated ketone and hydrohalogen acid, followed by the spontaneous formation of the monohalogenated ketal. This spontaneous formation of the monohalogenated ketal occurs as a result of the presence of hydrohalogen acid, a known catalyst for ketal formation.

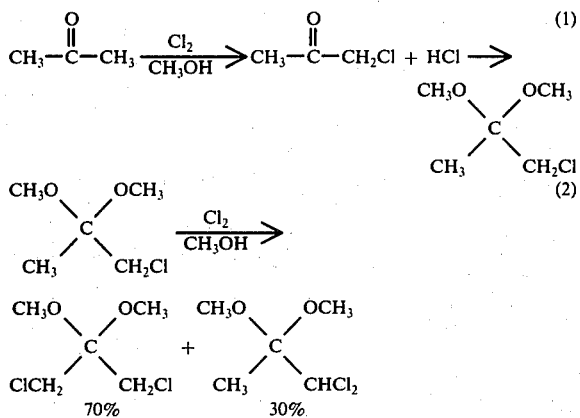

In other words, the initial halogenation step produces its own catalyst for the production of the monohalogenated ketal that ultimately results in high yields of symmetrically dihalogenated ketals. It is also believed reasonable to conclude that in view of the considerable amount of alcohol used, stable hypohalite, as well as the hydrohalogen acid, is also formed which is contributing to the initial halogenation as the primary halogenating agent. When a ketal is the starting material, the reaction occurs by direct halogenation. By direct halogenation is meant that the starting materials comprise a ketal, halogenating agent, etc., as previously exemplified. Therefore no ketal intermediate is formed as when the starting material is a ketone. The selectivity is maintained by virtue of the naturally sterically hindered molecule.

Typical ketones that may be used in this process cover a rather broad spectrum. They may be selected from compounds of the formula:

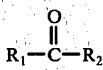

wherein $R_1$ and $R_2$ may be a straight or branched chain alkyl group of from 1 to 20 carbon atoms, such as acetone, 2-butanone, 1-propanone, 2-propanone, 2-pentanone, 3-pentanone, 2-hexanone, 3-hexanone, 2-heptanone, 3-heptanone, 4-heptanone, methylisopropyl ketone, ethyl isopropyl ketone, methyl isobutyl ketone, and the like.

Typical ketals that may be used in the process of the instant invention are selected from components having the formula:

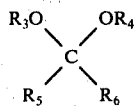

wherein $R_5$ and $R_6$ are the same as $R_1$ and $R_2$ which have been previously defined. $R_3$ and $R_4$ may be a straight chain alkyl group of from 1 to 20 carbon atoms, $R_3$ and $R_4$ may further be taken together to form a ring having from 2 to 4 carbon atoms. Examples of ketals that may be used are the dimethoxy ketals or the ethylene glycol ketals of the ketones mentioned above, viz. acetone, 2-butanone, etc. Also the propylene and the 2,3-butylene glycol ketals of the above-mentioned ketones may be used as well.

The preferred solvents however are the mono and polyhydric alcohols. As aforestated, the ratio of alcohol to ketone or ketal is critical and must be present in excess of at least 5:1. The alcohol/ketal-ketone ratio may vary from 5:1 to 20:1, preferably from 10:1 and most preferably 5:1. The use of an excess of alcohol decreases the decomposition products to practically nil and insures the obtention of predominately selectively and symmetrically dihalogenated products. While any mono and polyhydric alcohols having from 1 to 5 carbon atoms are generally usable in the instant invention, the most preferred alcohols are those wherein the number of hydroxyl groups is equal to the number of carbon atoms and each carbon atom is hydroxylated. Examples of the most preferred alcohols include methanol, ethylene glycol, glycerol, sorbitol. Alcohols higher than glycerol are generally solids, therefore it will be necessary that heat be applied to start the reaction.

Alcohols such as ethanol, 2,3-butanediol, and propylene glycol are also within the scope of this invention, however, some oxidation of the alcohol will occur. Tolerable amounts of alcohol oxidation will not appreciably affect the reaction. However, clean reactions, i.e. no alcohol oxidation, are obtained when the preferred alcohols are used.

The preferred alcohols are believed to form hypohalites which participate in the initial halogenation by providing either the chloronium or bromonium ions. In addition, it has been found that at the end of the reaction the starting alcohol is reformed from its hypohalite. This reformation is believed to occur either during or as a result of the halogenation step.

Although this invention is preferably carried out at ordinary conditions of temperature and pressure, a wide range of temperatures can be used, i.e. from about 0° 80° C, preferably 20° to 40° C and most preferably 25° to 30° C and from about 1 to about 10 atmospheres of pressure.

The solvents, as previously stated, may be selected from mono or polyhydric alcohols. Elsewhere in the specification the criticality of the alcoholic solvents has been discussed.

The proportion of chlorine or bromine used will depend upon the degree of halogenation desired. Generally, the molar ratio of chlorine or bromine to ketone or ketal will range from about 1:1 to about 5:1.

The reaction should be carried out with moderate stirring accompanied by a slow introduction of halogen in order to avoid possible explosions that may be caused by high concentrations of hypohalite resulting from incomplete reactions of same with a ketone or ketal.

As aforestated, when a ketal or ketone is sterically hindered such that the dihalogenated product does not form, one obtains a selectively monohalogenated ketal or ketone according to the process of the instant invention. All the process conditions are the same as when preparing the symmetrical dihalogenated product. The compounds treated by the process of the instant invention are of the formula:

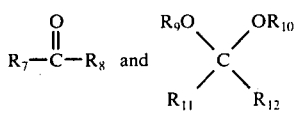

wherein each of $R_7$, $R_8$, $R_{11}$, and $R_{12}$ can be a branched chain alkyl group of from 3 to 20 carbon atoms, an alkylaryl or arylalkyl group wherein the alkyl moiety is a straight or branched chain of from 1 to 20 carbon atoms, phenyl, $R_7$, $R_8$, $R_{11}$, and $R_{12}$ may further be taken together to form a cycloalkyl ring having at least 6 carbon atoms; provided that when either of the pairs of $R_7$, $R_8$ or $R_{11}$, $R_{12}$ is a branched chain, phenyl, cycloalkyl, arylalkyl or alkylaryl as defined above, the other grouup is a straight chain alkyl group of from 1 to 20 carbons. $R_9$ or $R_{10}$ is a straight chain alkyl group of from 1 to 20 carbon atoms, $R_9$ and $R_{10}$ may further be taken together to form a ring having from 2 to 4 carbon atoms. Examples of compounds falling within the above definition are the following, 1-phenyl-3-cyclohexyl acetone, cyclohexyl acetophenone, 1,3-dicyclohexyl acetone, cyclohexyl methyl ketone, 1-cyclohexyl acetone, 4-cyclohexyl-2-butanone, 1-cyclohexyl-2-butanone, 3-cyclohexyl-2-butanone. The ketals that are useful in the instant process correspond to the dimethoxy, ethylene glycol, propylene and 2,3-butylene glycol ketals of the above-mentioned ketones.

If desired, these monohalogenated ketals may be hydrolyzed, under acid conditions, to the monohalogenated ketones.

The acids used to accomplish the hydrolysis of the mono or dihalogenated ketals can be any of the conventional mineral acids such as hydrochloric, sulfuric, phosphoric, chloric, chlorous, hydrobromic, hydrofluoric, sulfurous, di- and trifluoroacetic. Generally, any acid containing an electron withdrawing group may be used. The acid conditions contemplated herein are strong acid conditions, i.e., undiluted acid.

The following Examples are intended to be illustrative and in no way are to be construed as limiting the invention.

EXAMPLE 1

The following reactions illustrate the selectivity of halogenation as realized by the invention. In each case the reaction is accomplished by bubbling chlorine gas through an alcoholic solution of the respective ketones or ketals. All the reactions are conducted in a 250 ml, 3 neck flask at room temperature and atmospheric pressure accompanied by moderate agitation. The ratio of halogen to the ketone or ketal is 1:1 (molar basis) and the ratio of solvent to the ketone or ketal is about 5:1 (molar basis). The ensuing equations illustrate the yield and selectivity of the monochlorinated product. In all cases the product was extracted out with ether and the ether layer washed with water to remove ethylene glycol, when used. When methanol was used as a solvent, the resulting solution is either treated with water or subjected to a vacuum to remove the solvent. It is to be understood that further chlorination of the non-sterically hindered products will result in substantial amounts of symmetrically dichlorinated products.

(a)

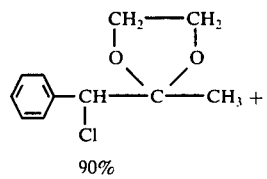

90%

+

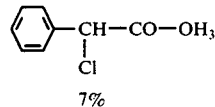

7%

This selectivity endured even though a 70% excess of chlorine was used.

In all the Examples the structures were determined by NMR.

NMR Data (in CDCl₃)

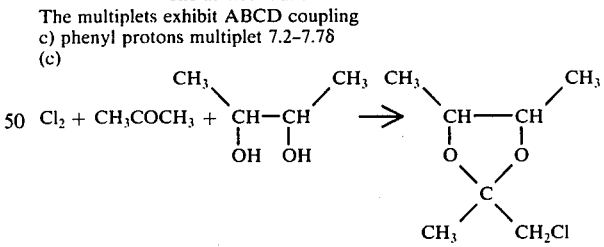

$CH_3$ peaks at 1.27δ
CHCl peaks at 4.87δ
Protons 1, 2, 3, 4 wide doublet at 3.84δ
Phenyl protons at 7.35δ
(b)

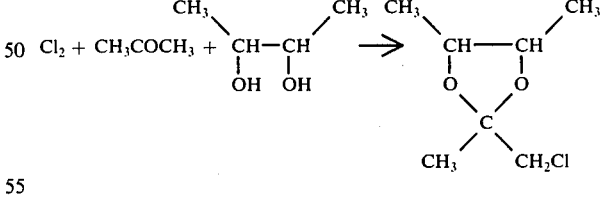

100%

NMR Data (in CDCl₃)

a) $CH_2Cl$ one peak at 3.75δ
b) Protons 1, 2, 3, 4
  2 multiplets one at 3.79–4.00δ
  one at 4.00–4.25δ
The multiplets exhibit ABCD coupling
c) phenyl protons multiplet 7.2–7.7δ
(c)

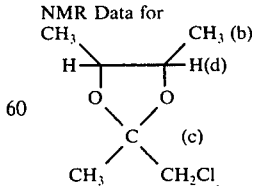

88%

NMR Data for

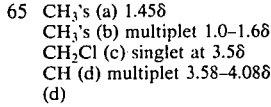

(a)
$CH_3$'s (a) 1.45δ
$CH_3$'s (b) multiplet 1.0–1.6δ
$CH_2Cl$ (c) singlet at 3.5δ
CH (d) multiplet 3.58–4.08δ
(d)

-continued

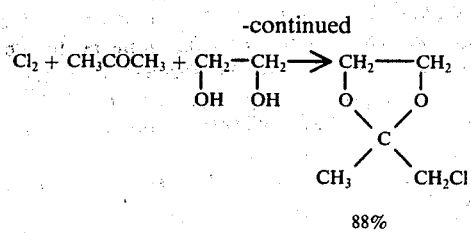

88%

NMR Data (in CDCl₃)

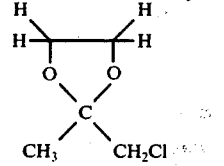

[Proton ratio 3:2:4] CH₃ protons singlet at 1.43δ
CH₂Cl protons singlet at 3.51δ
CH₂ protons singlet at 4.01δ

(e)
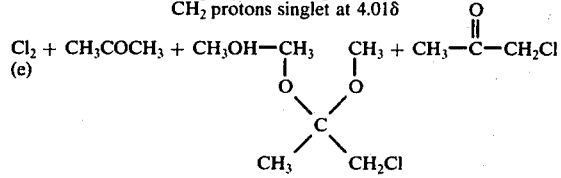

CH₃O singlet 3.15δ
CH₂Cl singlet 3.45δ
CH₃ singlet 1.28δ
(f)

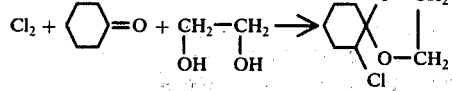

NMR Data

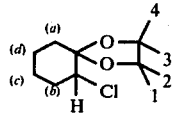

CH₂ (a) and (b) multiplet 1.7–2.3δ
CH₂ (c) and (d) large peak 1.2–1.7δ
CHCl multiplet 3 major peaks at 3.8, 4.0, 4.05δ + minor peaks
Protons 1, 2, 3, 4,
The ratio was 4:4:5
The chlorination of the following ketals was also investigated:
*(g)

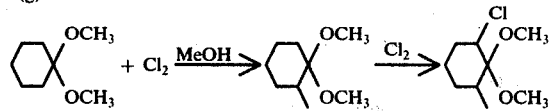

NMR data (in CDCl₃)

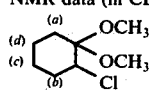

CH₃O singlet at 3.25δ
CHCl multiplet in the rgion of 4.22–4.6δ
CH₂ a, b, c, d multiplets in the region of 1.74–2.85δ
*(h)

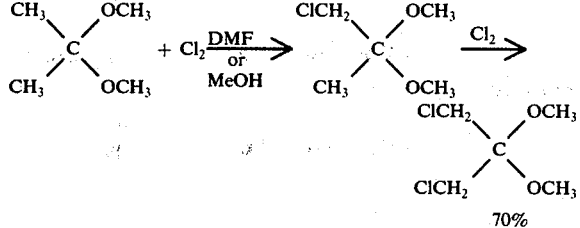

70%

*Reactions (g) and (h) are illustrative of situations where the second chlorination step was carried out resulting in symmetrically dichlorinated ketals.

It is also worthy to note that the symmetrically dihalogenated isomeric products are easily separable from from the unsymmetrical isomers. Separation is accomplished by crystallization at about −70° C. This has heretofore been relatively impossible or at best extremely difficult.

EXAMPLE 2

Into a 250 ml, 3 neck flask equipped with mechanical stirrer there were placed 11 grams of acetone and 110 mls CH₃OH; chlorinated slowly at 25° C. After one hour the acetone dichlorodimethyl ketal began to crystallize out of solution. The reaction mixture was monitored via NMR until the CH₃ peak for

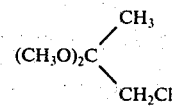

was present in small amounts. The chlorination was stopped and the mixture cooled to −70° C. 11.6 grams of dichlorinated product were crystallized out. The filtrate upon removal of CH₃OH consisted of mixtures of chlorinated isomers.

NMR Data in CDCl₃

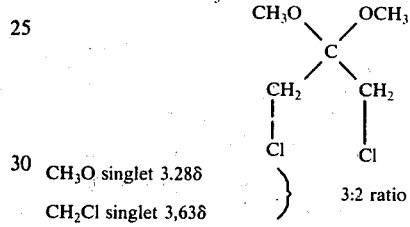

CH₃O singlet 3.28δ
CH₂Cl singlet 3,63δ      } 3:2 ratio

A similar reaction was carried out using 16 gm (0.28 mole) of acetone, 100 ml of ethylene glycol and 80 gms (1.1 mole) of Cl₂. The solution, after reaction, was extracted according to Example 1. The products were obtained in 93% yield (total) and in a ratio of 1:0.7.

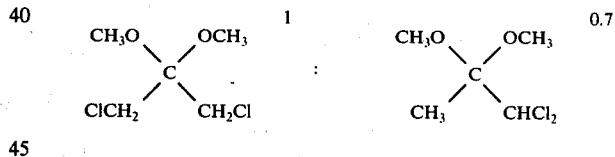

EXAMPLE 3

Example 2 was repeated with the sole exception that the chlorination was carried out at 5° C. This resulted in a yield of 14 grams of the dichlorinated acetal.

EXAMPLE 4

Into a 250 ml, 3 neck flask equipped with mechanical stirrer there were placed 60 grams 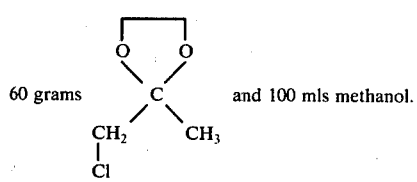 and 100 mls methanol.

0.11 mole of Cl₂ gas was bubbled in slowly, the reaction mixture cooled to −70° C and 13.5 g of dichlorinated ketal were obtained.

NMR Data

-continued

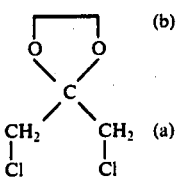

CH₂ (a) singlet 3.68δ
CH₂ (b) singlet 4.00δ

EXAMPLE 5

The following reaction illustrates the necessity of having steric hindrance in the molecule so that high yields of the symmetrical dichlorinated product are obtained.

In accordance with Example 1, 24 grams of

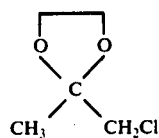

were chlorinated with 0.4 moles of $Cl_2$ in 150 ml of ethylene glycol. The chlorination continues until a yellow color persists (The yellow color is indicative of slow and difficult chlorination). The reaction mixture is extracted with ether and the ether layer distilled. A total of 54 grams of product is obtained, 5 grams of which is the dichlorinated ketal which distills over first.

EXAMPLE 6

Following the procedure of Example 2, 11.6 gm (0.2 mole) acetone and 110 ml ethylene glycol are placed in a 250 ml 3-necked flask and 0.4 mole of $Br_2$ is added in 0.2 mole portions (the second 0.2 mole portion being added at 60°–65° C). The layers formed were then separated and extracted (as described in Example 1). Total product(s) collected in 66% yield wherein the ratio of

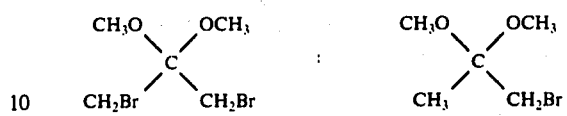

is 3.7 : 1.

EXAMPLE 7

The process of Example 6 was followed with the exception that 11.6 gms of acetone, 100 ml $CH_3OH$, and 65 gm of $Br_2$ were used. The following products were collected:

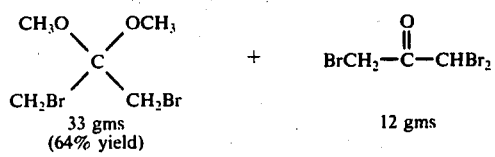

EXAMPLES 8 – 15

The following examples will illustrate the effect of steric hindrance upon the procurement of symmetrically dihalogenated product. The procedure is basically that of Example 1. The results obtained appear in tabulated form below.

TABLE 1

| Example No. | Ketone (gms) | Solvent (ml) | Halogen (moles) |
|---|---|---|---|
| 8 | $(CH_3)_2CH-\underset{\underset{O}{\|\|}}{C}-CH(CH_3)_2$ - 25 | ethylene glycol - 140 | $Cl_2$ - 0.50 |
| 9 | $CH_3-\underset{\underset{O}{\|\|}}{C}-CH(CH_3)_2$ - 25 | ethylene glycol - 160 | $Cl_2$ - 0.37 |
| 10 | $CH_3-\underset{\underset{O}{\|\|}}{C}-CH(CH_3)_2$ - 15.6 | methanol - 200 | $Cl_2$ - 0.20 |
| 11 | $CH_3CH_2-\underset{\underset{OH}{\|}}{C}-CH(CH_3)_2$ - 18 ** | ethylene glycol - 100 | $Cl_2$ - 0.28 |
| 12 | Ph$-\underset{\underset{O}{\|\|}}{C}-CH_3$ - 12 | ethylene glycol - 100 | $Br_2$ - 0.12 |
| 13 | $(CH_3)_3-C-\underset{\underset{O}{\|\|}}{C}-CH_3$ - 20 | ethylene glycol - 120 | $Cl_2$ - 0.53 |
| 14 | $(CH_3)_3-\underset{\underset{H}{\|}}{\overset{\overset{H}{\|}}{C}}-\underset{\underset{O}{\|\|}}{C}-CH_3$ - 20 | ethylene glycol - 120 | $Br_2$ - 0.20 |
| 15 | (ketal structure with $CH_3$ and $CH(CH_3)_2$) - 10.5 | ethylene glycol - 100 | $Br_2$ - 1.1 |

| Example No. | Product(s) (Ratio) |
|---|---|
| 8 | $(CH_3)_2-CH-\underset{\underset{O}{\|\|}}{C}-\underset{\underset{Cl}{\|}}{C}-(CH_3)_2$* |

TABLE 1-continued

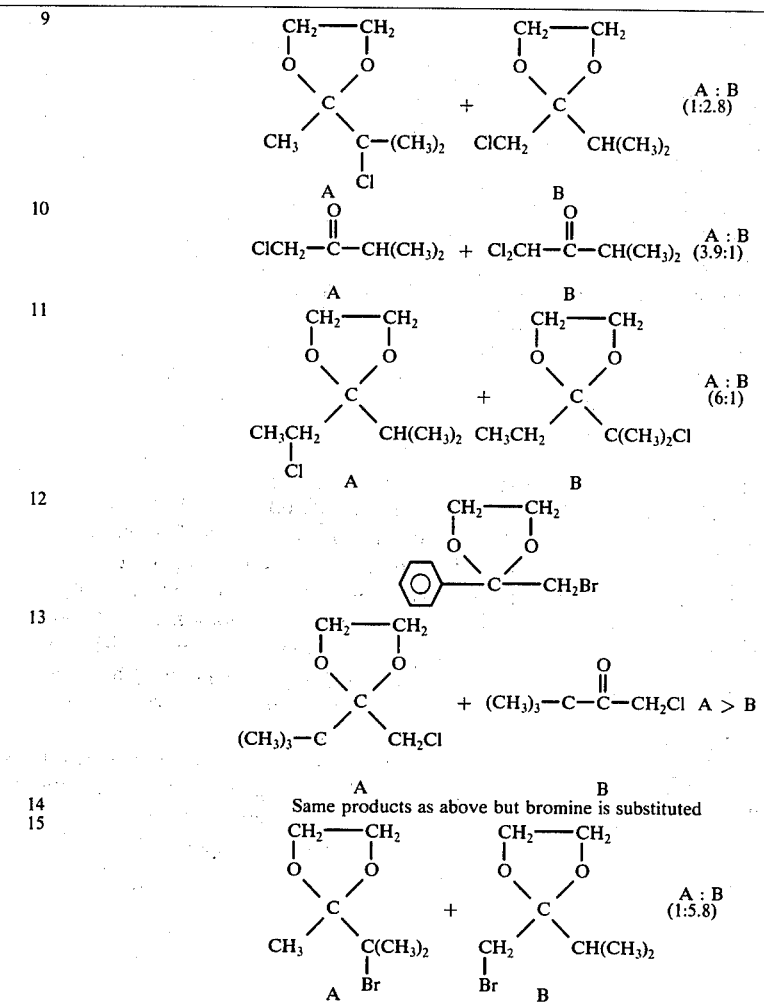

*no corresponding ketal was formed due to excessive steric hindrance.
**was oxidized to the ketone first by the halogen
NOTE:
Although steric hindrance prevents formation of the symmetrical dihalogenated product, it will be noted that the halogenation is selective as previously described.

What is claimed is:

1. A method of preparing selectively and symmetrically dihalogenated ketals consisting essentially of treating with a halogen selected from the group consisting of chlorine and bromine, compounds of the formula:

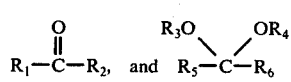

wherein each of $R_1$, $R_2$, $R_5$, and $R_6$ is a non-sterically hindered straight or branched chain alkyl group of from 1 to 20 carbon atoms; each of $R_3$ and $R_4$ is a straight or branched chain alkyl group of from 1 to 20 carbon atoms, or $R_3$ and $R_4$ may further be taken together to form a ring having from 2 to 4 carbon atoms; said halogenation occurring at the carbon atoms alpha to the ketal or carbonyl group; said treatment being in an organic solvent selected from the group consisting of monohydric and polyhydric alcohols wherein each C-H group of said alcohol has an hydroxyl group attached thereto and the ratio of said solvent to ketone or ketal is from about 5:1 to about 20:1; the molar ratio of said halogen to ketone or ketal is from about 2:1 to about 5:1; and at a temperature of from about 0° to about 80° C.

2. A method for the preparation of selectively and symmetrically dichlorinated ketals which consists essentially of treating with gaseous chlorine, compounds of the formula:

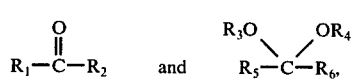

wherein each of $R_1$, $R_2$, $R_5$, and $R_6$ is a non-sterically hindered straight chain alkyl group of from 1 to 20 carbon atoms; each of $R_3$ and $R_4$ is a straight chain alkyl group of from 1 to 20 carbon atoms, or $R_3$ and $R_4$ may further be taken together to form a ring having from 2 to 4 carbon atoms when each of $R_5$ and $R_6$ is a straight chain alkyl group of 1 to 20 carbon atoms; in methanol, wherein the ratio of methanol to ketone or ketal is from 5:1 to about 20:1; said chlorination occurring at the carbon atoms alpha to the ketal or carbonyl group; the molar ratio of said chlorine to ketone or ketal is from about 2:1 to about 5:1; and at a temperature of about 20° to 40° C.

3. A method according to claim 1 wherein said organic solvent contains from 1 to 5 carbon atoms.

4. A method according to claim 1 wherein the ketone is selected from the group consisting of acetone, 2-butanone, 1-propanone, 2-propanone, 2-pentanone, 3-pentanone, 2-hexanone, 3-hexanone, 2-heptanone, 4-heptanone, methylisopropyl ketone, ethyl isopropyl ketone and methyl isobutyl ketone.

5. A method according to claim 1 wherein the ketal is selected from the group consisting of the dimethoxy, ethylene glycol, propylene glycol and 2,3-butylene glycol ketals of acetone, 2-butanone, 1-propanone, 2-propanone, 2-pentanone, 3-pentanone, 2-hexanone, 3-hexanone, 2-heptanone, 3-heptanone, 4-heptanone, methylisopropyl ketone, ethyl isopropyl ketone, and methyl isobutyl ketone.

6. A method according to claim 3 wherein the ketone is selected from the group consisting of acetone, 2-butanone, 1-propanone, 2-propanone, 2-pentanone, 3-pentanone, 2-hexanone, 3-hexanone, 2-heptanone, -3-heptanone, 4-heptanone, methylisopropyl ketone, ethyl isopropyl ketone and methyl isobutyl ketone.

7. A method according to claim 3 wherein the ketal is selected from the group consisting of the dimethoxy, ethylene glycol, propylene glycol and 2,3-butylene glycol ketals of acetone, 2-butanone, 1-propanone, 2-propanone, 2-pentanone, 3-pentanone, 2-hexanone, 3-hexanone, 2-heptanone, 3-heptanone, 4-heptanone, methylisopropyl ketone, ethyl isopropyl ketone, and methyl isobutyl ketone.

8. A method according to claim 1 wherein the alcohols are selected from the group consisting of methanol, ethylene glycol, glycerol and sorbitol.

9. A method according to claim 8 wherein the ratio of alcohol to ketone or ketal is from about 5:1 to about 10:1.

* * * * *

UNITED STATES PATENT OFFICE
CERTIFICATE OF CORRECTION

Patent No. 4,067,886              Dated   January 10, 1978

Inventor(s)  Robert C. Reardon, Jr. et al.

It is certified that error appears in the above-identified patent and that said Letters Patent are hereby corrected as shown below:

Col. 7, line 16:  "grouup" should be -- group --.

Col. 8, lines 10-13:

change 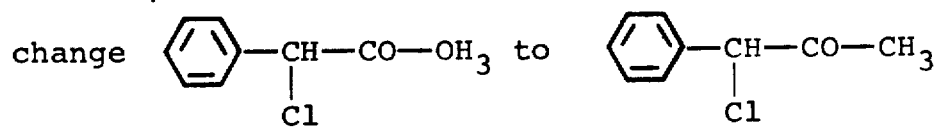

Col. 13, Example 11, Compound A:

change 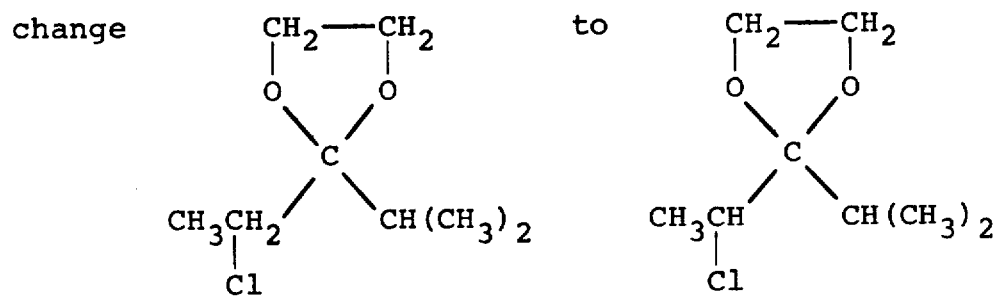

Signed and Sealed this

Thirtieth Day of May 1978

[SEAL]

Attest:

RUTH C. MASON
Attesting Officer

LUTRELLE F. PARKER
Acting Commissioner of Patents and Trademarks